(12) United States Patent
Kazakevich

(10) Patent No.: US 6,921,920 B2
(45) Date of Patent: Jul. 26, 2005

(54) SOLID-STATE LIGHT SOURCE

(75) Inventor: Yuri Kazakevich, Andover, MA (US)

(73) Assignee: Smith & Nephew, Inc., Memphis, TN (US)

(*) Notice: Subject to any disclaimer, the term of this patent is extended or adjusted under 35 U.S.C. 154(b) by 261 days.

(21) Appl. No.: 09/944,495

(22) Filed: Aug. 31, 2001

(65) Prior Publication Data

US 2003/0042493 A1 Mar. 6, 2003

(51) Int. Cl.[7] .............................................. H01L 29/267

(52) U.S. Cl. ........................ 257/81; 257/88; 600/178; 600/182

(58) Field of Search ................................ 600/101, 108, 600/160, 178, 179, 181, 182; 257/79, 81, 88

(56) References Cited

U.S. PATENT DOCUMENTS

| 3,676,671 | A | * | 7/1972 | Sheldon .................... 257/71 R |
|---|---|---|---|---|
| 4,106,078 | A | | 8/1978 | Inoue |
| 4,883,333 | A | | 11/1989 | Yanez |
| 5,036,834 | A | | 8/1991 | Sugiyama et al. |
| 5,143,435 | A | | 9/1992 | Kikuchi |
| 5,237,403 | A | | 8/1993 | Sugimoto et al. |
| 5,491,765 | A | | 2/1996 | Matsumoto |
| 5,742,115 | A | * | 4/1998 | Gertsenshteyn ............. 313/365 |
| 5,746,494 | A | | 5/1998 | Koeda et al. |
| 5,751,869 | A | * | 5/1998 | Li et al. ....................... 385/33 |
| 5,823,943 | A | | 10/1998 | Tomioka et al. |
| 5,888,194 | A | | 3/1999 | Utsumi et al. |
| 5,971,576 | A | | 10/1999 | Tomioka et al. |
| 6,331,156 | B1 | * | 12/2001 | Haefele et al. ............. 600/179 |
| 6,371,909 | B1 | | 4/2002 | Hoeg et al. |
| 6,485,414 | B1 | * | 11/2002 | Neubergerq ................ 600/182 |
| 6,491,618 | B1 | * | 12/2002 | Ganz ............................. 600/3 |
| 6,498,948 | B1 | * | 12/2002 | Ozawa et al. ............... 600/476 |
| 6,516,216 | B1 | * | 2/2003 | Fontenot et al. ............ 600/473 |
| 6,518,600 | B1 | * | 2/2003 | Shaddock .................... 257/98 |
| 6,528,954 | B1 | * | 3/2003 | Lys et al. .................... 315/291 |
| 6,584,335 | B1 | * | 6/2003 | Haar et al. .................. 600/322 |
| 6,692,431 | B2 | * | 2/2004 | Kazakevich ................ 600/178 |
| 6,696,703 | B2 | * | 2/2004 | Mueller-Mach et al. ...... 257/98 |
| 6,793,374 | B2 | * | 9/2004 | Begemann .................. 362/294 |

FOREIGN PATENT DOCUMENTS

| GB | 2339926 | 2/2000 |
|---|---|---|
| WO | 96/05693 | 2/1996 |
| WO | WO 01/49164 A1 | 7/2001 |
| WO | 01/49164 | 7/2001 |

OTHER PUBLICATIONS

"LUXEN™ Lumileads Announces Breakthrough for Better White LEDs"; Lumileds Lighting, LLC; May 29, 2001, San Jose, CA.

"NICHIA Surface Mount Type LED Light Emitting Diode"; Nichia Corporation; Product Guide; NSCx Series, NSSx Series, NSCM315C (Full Color).

"Vertical cavity nitride system emits blue laser light"; Electron Engineering Times; Oct. 4, 1999; p. 65.

"Virtual Rays Enlighten Lamp Designs" Photonics Design & Solutions; Photonics Spectra; Sep. 1999; pp. 123–130.

(Continued)

Primary Examiner—Sara Crane
(74) Attorney, Agent, or Firm—Fish & Richardson P.C.

(57) ABSTRACT

A solid-state light source includes a semiconductor light source for emitting light and an optical system having a fiber optic element. The fiber optic element has an input for receiving emitted light from the semiconductor light source. The fiber optic element also has an output for emitting light received from the solid-state light source. The semiconductor light source and the fiber optic element in aggregate form an illumination path.

34 Claims, 16 Drawing Sheets

OTHER PUBLICATIONS

PCT Notification of Transmittal of The International Search Report or the Declaration for International Application No. PCT/US 01/27110 filed Aug. 26, 2002.

"Automotive Exterior Lighting From Filaments To"; Jeffrey T. Remillard, Michael A. Marinelli, and Timothy Fohl; Optics & Photonics News; Aug. 1999; pp. 40–43.

"HP Introduces White LEDs with Color–Temperature Grading"; Electronic Components; Hewlett Packard; Palo Alto, California; Mar. 15, 1999.

"Color the market blue"; Marketwatch; Laser Focus World; Sep. 1999; p. 57.

\* cited by examiner

SOLID-STATE LIGHT SOURCE

TECHNICAL FIELD

This invention relates to solid-state light sources for providing illumination.

BACKGROUND

Portable light sources are used to selectively illuminate dimly lit or dark environments (e.g., miner's helmets, flashlights). Other light sources are used to provide higher intensities of light to specific areas for observation (e.g., microscopes). Typically, these light sources are incandescent or fluorescent. Some light sources require high intensity of light and occupy a small area.

Light sources are also used in endoscopy (e.g., medical, industrial). Medical endoscopes are used to inspect dark regions within the body (e.g., cavities, joints) during surgery (such as laparoscopic/thoracoscopic surgery) through a small puncture. Typically, the endoscope includes a rigid or flexible elongated insertion tube equipped with a set of optical fibers that extend from a proximal handle through the insertion tube to the distal viewing tip of the endoscope. An external light source provides light to the optical fibers via a cable that attaches to the handle (e.g., at a post on the side of the handle) of the endoscope.

Other lights sources are used in surgical instruments (e.g., lighted surgical forceps, light wands, dental probes).

SUMMARY

The invention is related to a solid-state light source for providing light.

In a general aspect of the invention, the solid-state light source includes a semiconductor light source for emitting light and a fiber optic element. The fiber optic element has an input for receiving emitted light from the semiconductor light source. The fiber optic element also has an output for emitting light received from the semiconductor light source. The semiconductor light source and the fiber optic element in aggregate providing an illumination path.

In another aspect of the invention, the solid-state light source provides light to an endoscope and includes a semiconductor light source for emitting light and an optical system having an optical element. The optical element has an input for receiving emitted light from the semiconductor light sources and an output for receiving light from the optical element and configured to be received by the endoscope. The semiconductor light source and the fiber optic element in aggregate providing an illumination path.

Embodiments of these aspects may include one or more of the following features. The fiber optic element is in the form of a plurality of fiber optic lines, each of the plurality of fiber optic lines receiving the emitted light from the semiconductor light source. The fiber optic lines are in the form of a bundle. The semiconductor light source has multiple surfaces and each surface emits light to a corresponding fiber optic bundle. The solid-state light source can also include multiple semiconductor light sources and an array of fiber optic lines so that each fiber optic line is aligned with a corresponding semiconductor light source.

The semiconductor light source may be of different configurations (e.g., a light emitting diode (LED), a laser diode, a vertical cavity surface emission laser). The semiconductor light sources can be configured to emit a blue light or an ultraviolet light. The phosphor layer is located in the illumination path of the semiconductor light source. Each semiconductor light source is in contact with a phosphor layer or the phosphor layer can be located at a distal end of the fiber optic element. In other embodiments, the semiconductor light source includes a first light emitting diode (LED) configured to emit blue light, a second LED configured to emit red light and a third LED configured to emit green light, an overlapping light from each LED producing white light. The solid-state light source includes a mixer positioned to receive light from the first LED, the second LED, and the third LED and it is also positioned to transmit the overlapping light to the fiber optic line. The semiconductor light source can also include a fourth LED configured to emit yellow light and the mixer receives the light emitted from the fourth LED.

In another semiconductor light source configuration, the solid-state light source also includes an encasement having an aperture positioned over the semiconductor light source, a gel located within the encasement and the fiber optic element is inserted through the aperture and gel. In still another embodiment, the solid-state light source includes an ohmic contact positioned on a top surface of the semiconductor light source and where the fiber optic bundle has a spliced-end to receive the ohmic contact.

Other embodiments include having various lens configurations. These embodiments include a lens for receiving light from the semiconductor source. The semiconductor light source is optically aligned with the lens and the lens is optically aligned with the fiber optic line. The semiconductor light source is positioned in a first optical conjugate plane from the lens and the fiber optic line is positioned in a second optical conjugate plane from the lens. Instead of one lens, the solid-state light source can include an array of lenses. Likewise, instead of one fiber optic line, the solid-state light source can include an array of fiber optic lines corresponding to each of the lenses. Moreover, instead of one semiconductor light source, the solid-state light source can include an array of semiconductor light sources corresponding to each of the lenses.

In other embodiments, the solid-state light source includes an array of lenses configured to collimate light from a corresponding array of semiconductor light sources and a focusing lens configured to focus a collimated light from the array of lenses. The focusing lens focuses the collimated light onto a light guide.

The first aspect has a further embodiment of having the output of the fiber optic element configured to be received by an endoscope.

Among other advantages of each aspect, the solid-state light source provides better lumen per watt output compared to incandescent lamps. The solid-state light source concentrates light in a small area while providing high luminous emittance. Also, the semiconductor light source more efficiently couples light energy into an optical element (e.g., optic fiber). In general, the solid-state light source is compact and consumes less power. In addition, the solid-state light source responds to changes in applied voltage more quickly than an incandescent lamp or an arc lamp.

DETAILED DESCRIPTION

Figure 1:
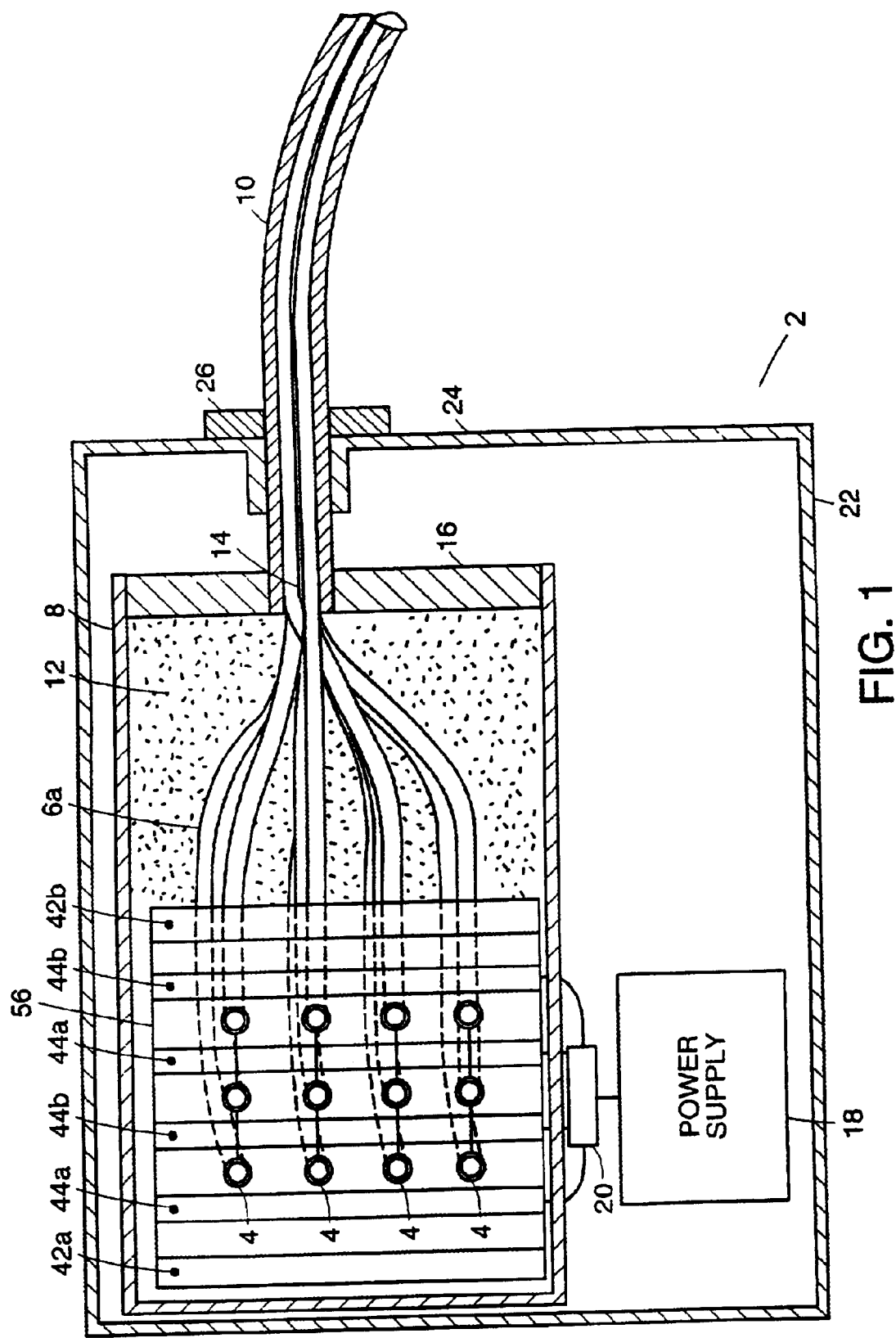
FIG. 1 is a cross-sectional schematic representation of one embodiment of a solid-state light source.
Figure 3:
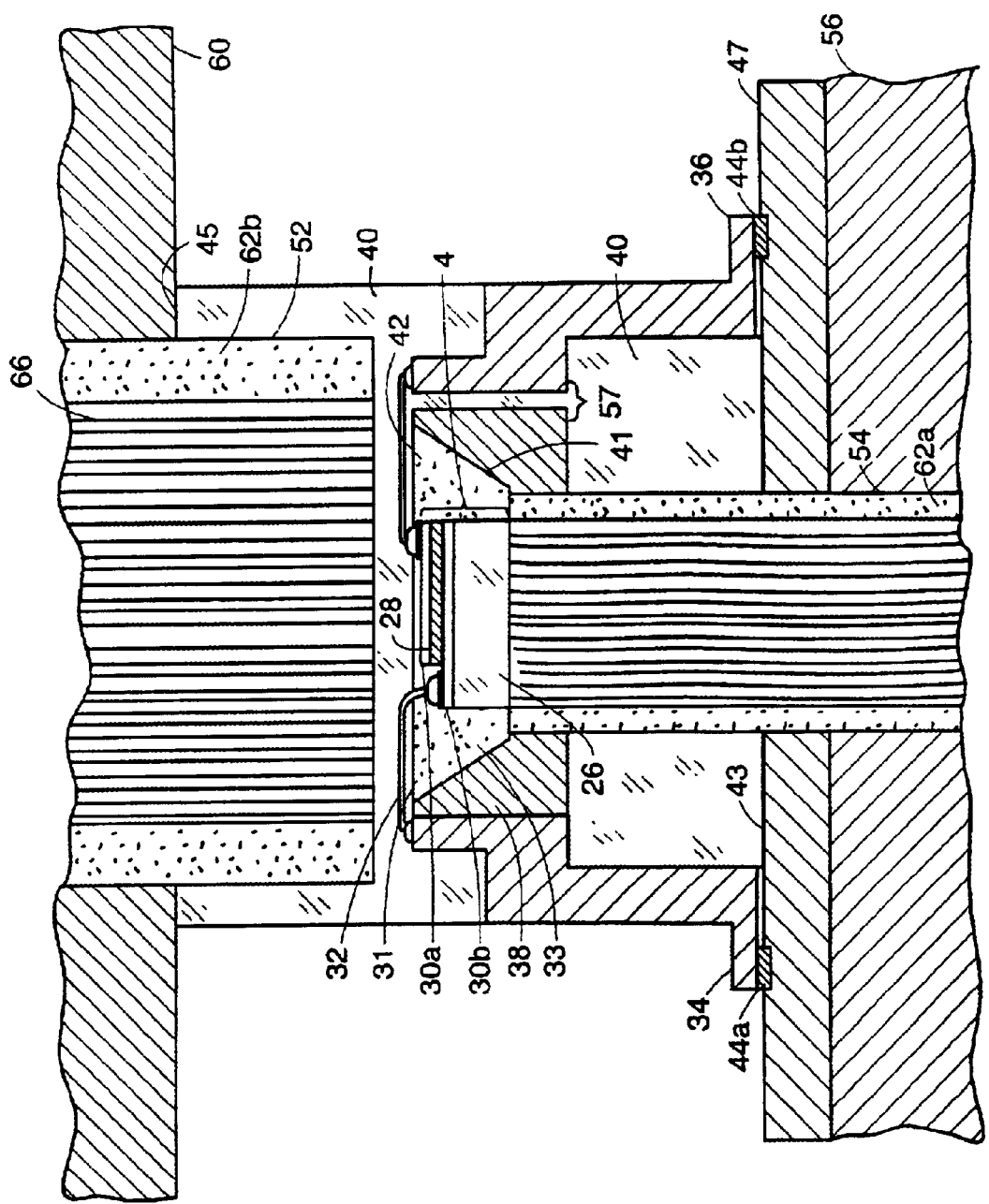
FIG. 3 is an enlarged cross-sectional side view of a portion of the solid-state light source shown in FIG. 1.

Referring to FIG. 1, a solid-state light source 2 includes light emitting diode (LED) chips 4 (referred herein as LEDs). LEDs 4 are arranged in a 4×3 array. Each LED 4, in operation, emits light to end regions of a corresponding pair of fiber optic bundles 6a and 6b (FIG. 3). In contrast to other forms of illumination sources (e.g., incandescent lamps), LEDs (and other such semiconductor light sources) provide better lumen per watt output and consume less power and space. LEDs also are more efficient than lamps in coupling light energy into fiber optic lines due to the small size and high luminosity of the LEDs.

LEDs 4 and fiber optic bundles 6a and 6b are encapsulated in an inner housing 8 using a potting compound 12 (e.g., silicone adhesive) so that the LEDs and fiber optic bundles are immobilized and hermetically sealed from an external environment. Fiber optic bundles 6a and 6b extend from the LEDs and are brought together into a single multi-bundle 14 at one end of inner housing 8. In this embodiment, multi-bundle 14 extends into and terminates at a wall 16 of inner housing 8. Solid-state light source 2 also includes a power supply 18 and a distribution circuit 20, which together supply power to each of the LEDs 4.

Inner housing 8 (including LEDs 4 and fiber optic bundles 6a and 6b) along with power supply 18 and distribution circuit 20 are enclosed within an outer enclosure 22. In this embodiment, outer enclosure 22 includes a wall 24 having an output connector 26 where a light guide 10 is secured and attached to multi-bundle 14 from inner housing 22.

In other embodiments, fiber optic bundles 6a and 6b are bundled together to form a single multi-bundle that extends continuously from housing 8 to a distal end 12 of light guide 10, thereby eliminating an optical transition that can contribute to reducing light transmission.

Figure 2B:
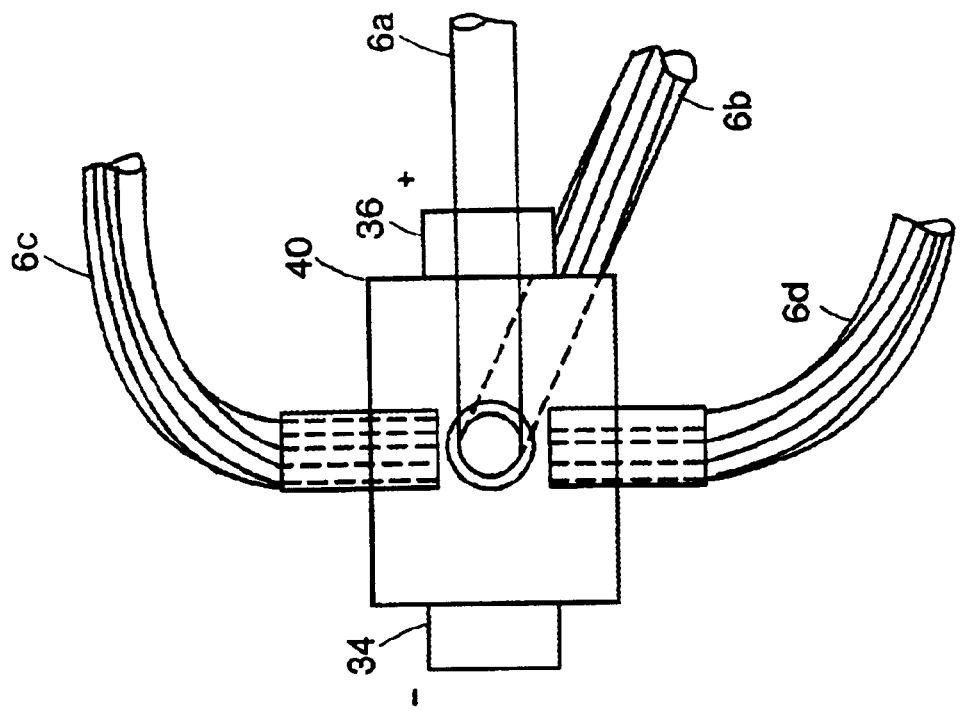
FIG. 2B is a top view of the LED and the set of fiber bundles.
Figure 2A:
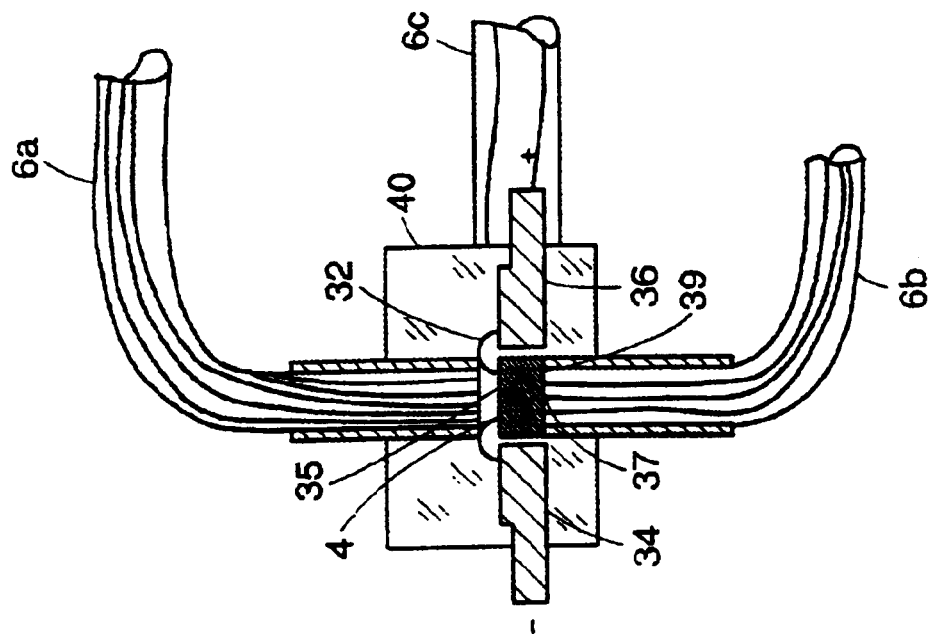
FIG. 2A is a cross-sectional side view of a light emitting diode (LED) and a set of fiber bundles.

Referring to FIGS. 2A and 2B, in still another embodiment, the light is collected from four surfaces of LED 4: a top surface 35, a bottom surface 37, a first side 39 and a second side opposite the first side (not shown). Normally, LEDs emit light in a 4π solid angle. Each surface emits light to a corresponding fiber optic bundle 6a–6d.

Referring to FIG. 3, each LED 4 has semiconductor conductor layers 30a and 30b grown or bonded to an optically transparent material 26 (e.g., sapphire). LED 4 has a light emitting region 28 sandwiched between two semiconductor layers 30a and 30b.

Each LED 4 is further encapsulated in a clear epoxy or plastic encasement 40 along with a reflector cup 38. Reflector cup 38 has reflective surfaces 41. Also, reflector cup 38 has a tapered-shape so that a bottom portion 33 of the reflector cup is narrower than a top portion 31. LED 4 is centered at the bottom 33 of reflector cup 38. The interior of reflector cup 38 is filled with clear silicone or gel material 42. Because the LEDs emit light in all directions, reflector cup 38 ensures that a substantial amount of the light emitted from the side surfaces of the LED are reflected toward the exposed face of fiber optic bundle 6b.

Fiber optic bundle 6b is wider than fiber optic bundle 6a in order to capture as much reflected light as possible. In other embodiments, without a reflector cup, fiber optic bundles 6b has a width similar to fiber optic bundle 6a.

Each LED 4 is also connected to a negative lead 34 and a positive lead 36. The leads 34 and 36 each protrude from the sides of epoxy encasement 40. The leads 34 and 36 are connected to LED 4 via ohmic contacts 32, for example, in the form of gold wires. Negative lead 34 abuts reflector cup 38 and is connected to a conductive bus 44a. Conductive bus 44a is insulated with a printed circuit board 47. Positive lead 36 is spaced from reflector cup 38 by a distance 57 and is connected to a conductive bus 44b. Conductive bus 44b is also insulated with printed circuit board 47. Each of conductive buses 44a and 44b carry electrical current from a power supply 18 via a distribution circuit 20 so that a forward current is applied to each LED 4. Power supply 18 contains multiple current sources and control circuitry to maintain the required forward currents needed to illuminate LEDs 4.

In this embodiment, LEDs 4 are square, approximately 0.25 mm per side. LEDs 4 suitable for use in this embodiment of solid-state source 2 can be obtained from Nichia Corporation of Tokushima, Japan, (part number NSCX or NSSx surface mount series). After obtaining LEDs 4 from the manufacturer, a hole is drilled into a top surface 45 of the epoxy encasement 40 of the LED to form a channel 52 for inserting optic fiber 6b. A second hole is drilled into a bottom surface 43 of epoxy encasement 40 to form a channel 54 for inserting optic fiber 6b. The holes are necessary to ensure that fiber optic bundles 6a and 6b are placed as close to LEDs 4 as possible to minimize light loss.

Fiber optic bundles 6a and 6b are 0.35 mm diameter and 0.7 mm diameter bundles, respectively, having preferably high Numerical Aperture (NA) (0.75 NA and above) glass fibers. Each glass fiber has a diameter of approximately 30–50 microns each. Fiber optic bundles 6a and 6b are assembled from loose fibers and bound together at the ends for instance. The loose fibers for this embodiment can be obtained from Schott-Foster, LLC of Auburn, N.Y. Alternatively, the bundle is fabricated using fused glass such as fiber light guides that are fine polished or made from other methods such as using fiber fusion technology. Fiber optic bundles 6a and 6b, suitable for this embodiment, can be obtained by INCOM, Inc. of Southbridge, Mass. The fibers are fabricated with a rectangular shaped cross-section to conform to the size and shape of the LED. In other embodiments, the fibers have a round shaped cross-section. In still other embodiments, single fibers (e.g., plastic fibers, quartz fibers) are used instead of fiber optic bundles.

Bottom surface 76 of each LED 4 is bonded to fiber optic bundles 6a with an optically clear bonding agent (e.g., Norland 61 from Norland Products, Inc. of North Brunswick, N.J.) so that each LED 4 is aligned relative to a corresponding one of fiber optic bundles 6a. By placing each LED 4 on each fiber optic bundle 6a, a maximum amount of light emitted from the LED is transferred into fiber optic bundles 6a and 6b and light losses are minimized. The bonding agent is an optically clear adhesive, which allows the light to travel to fiber optic bundles 6a without obstruction. A light entrance surface of fiber optic bundle 6b has an optical adhesive 64 (e.g., Norland 61 from Norland Products, Inc. of North Brunswick, N.J.) that secures fiber optic bundles 6b to LED 4.

Channel 54 continues through printed circuit board 47 through bottom plate 56 for receiving a corresponding one of the rectangular shaped fiber optic bundle 6a. A fiber end epoxy 62a is applied to fiber optic bundles 6a within bottom plate 56 to fill the gaps created when the rectangular shaped fiber-optic bundle fills the circular shaped channel. Fiber end epoxy 62a enables each plate channel to be completely filled with the optical fiber by ensuring that fiber optic bundles 6a are sealed and secured. Like bottom plate 56, a top plate 60 has similar channels 52 that contain fiber optical bundles 6b sealed with a fiber end epoxy 62b. Spacers 42a and 42b (FIG. 1) are positioned within and at opposite ends of internal housing 8 and between bottom plate 56 and top plate 60 to reduce stress on epoxy encasement 40.

Figure 4:
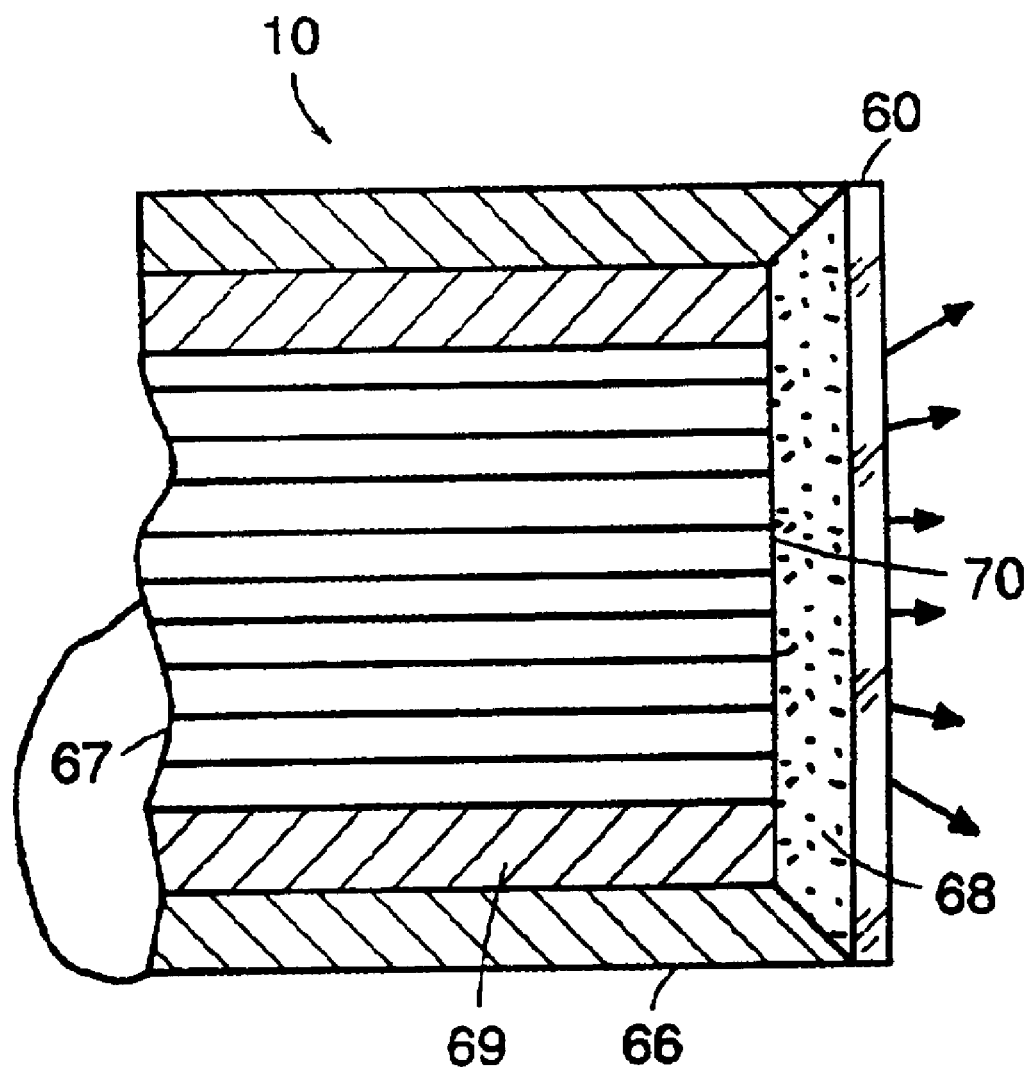
FIG. 4 is a cross-sectional side view of a light guide at a distal end of a light guide.

Referring to FIG. 4, at distal end 12 of light guide 10, multiple fibers 67 of light guide 10 are bound together and captured by a ferrule 69. A phosphor layer 68 (e.g., Yttrium Aluminum Garnet (YAG)) is placed over the light exiting face 70 of light guide 16. Phosphor layer 68 is surrounded by a protective sleeve 66 formed of stainless steel and covered by an optically transparent protective cover 60 (e.g., optical grade sapphire, optical glass).

When excited by an electrical current from power supply 18, the LEDs 4 emit a blue light. The blue light travels through fiber optic bundles 6a and 6b through multi-bundle 14, and on to distal end 12 of light guide 10. When the blue light passes through phosphor layer 68, the blue light excites the phosphor layer 68 causing it to fluoresce green and red light. The green light, the red light, and the blue light overlap and together form white light. In other embodiments, the phosphor layer can be applied directly to the surfaces of the LEDs. In other embodiments, additional LEDs emitting other light colors (e.g., yellow) can be added to form white light.

In the embodiment described above in conjunction with FIGS. 1–4, LEDs 4 were used as semiconductor light sources. However, in other embodiments, other semiconductor light sources can be used. For instance, the LEDs can be replaced with blue or UV laser diodes or vertical cavity surface emission lasers (VCSELs). Since the laser diode advantageously emits light directionally, as opposed to the LED, which emits light in all directions, the selection of fiber optics with high NA is less important. However, blue laser diodes and blue VCSELs are limited in availability, have a higher cost, have a low power output and have a short lifetime compared to LEDs.

Other semiconductor light sources use an ultraviolet (UV) LED along with a red-green-blue (RGB) phosphor layer to produce white light. When the UV light passes through the RGB phosphor layer, the phosphor layer emits a combined red, green, and blue light to form white light.

Other semiconductor light sources use blue, green, and red LEDs in combination to also generate white light. When the green, red, and blue LEDs are positioned relatively close together, the light from each LED overlaps. The overlap of the red, green, and blue light in the right proportion forms white light. Since there is not complete overlap of the red, green, and blue lights, the red, green, and blue lights and other combinations of these light colors can appear at the distal end of the light guide. To reduce this nonuniformity, the optical fibers are grouped in groups of three fibers (i.e., a trio), each trio carrying one of each of the red, blue, and green light. A diffuser (not shown) is typically added to the distal end of the light guide to add uniformity to the resultant light by mixing the remaining red, green and blue light that exists at the distal end.

Figure 5A:
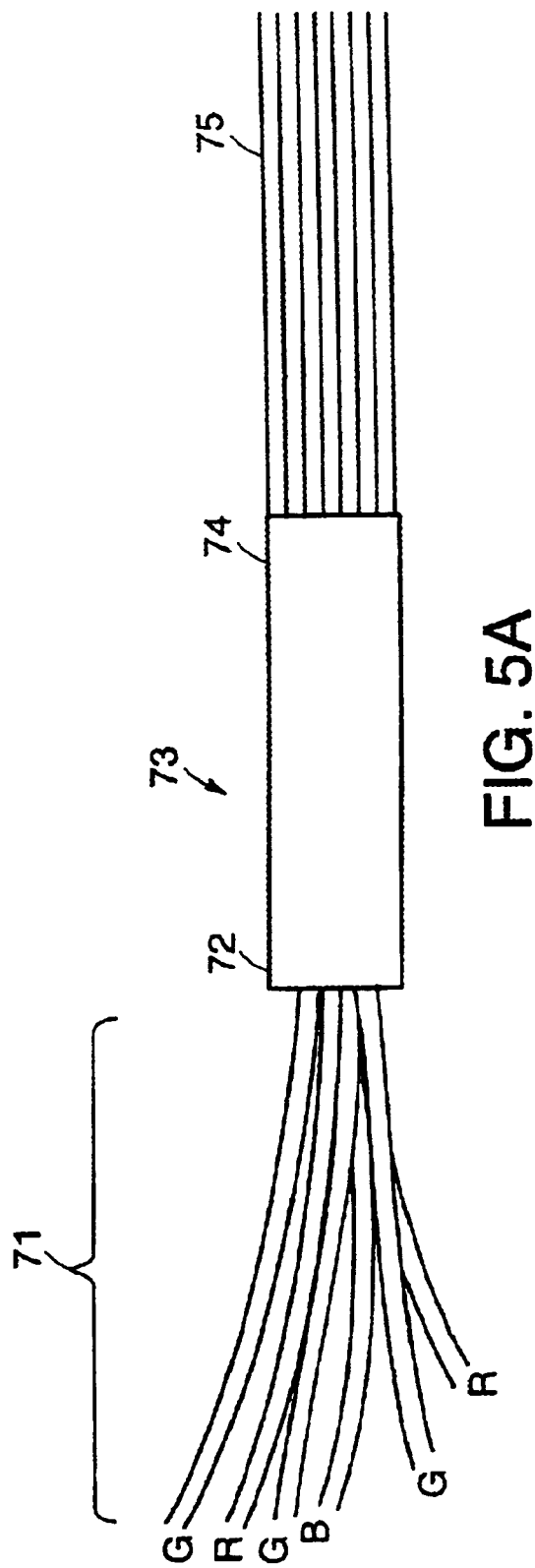
FIG. 5A is a cross-sectional side view of a mixing rod.
Figure 5B:
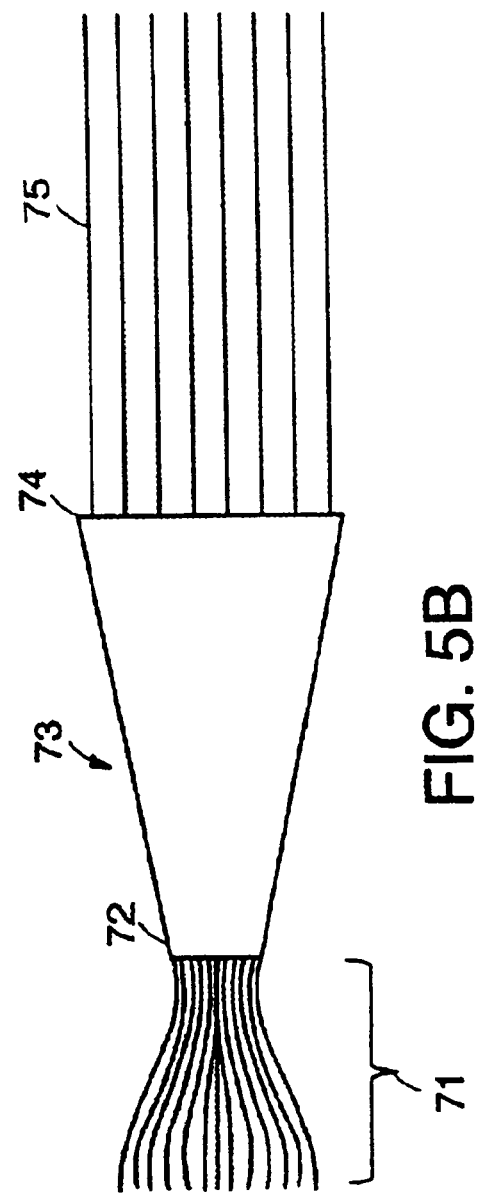
FIG. 5B is a cross-sectional side view of another mixing rod embodiment with a tapered-shape.

Other embodiments can have LEDs each emitting one of four colors (e.g., red, yellow, blue, and green) or each generating one of a multiple of colors in order to create the white light. Referring to FIG. 5A, a mixer with a square or hexagonal cross section can be added to a light guide 75 to mix the different colors of light to form white light. Other shaped cross sections may be used that facilitate mixing of the light colors. Each LED emits light to one fiber. Fibers 71 are attached to an input end 72 of mixer 73. Light guide 75 is attached to an output end 74 of mixer 77. As the different colors of light pass through mixer 73, the light colors are mixed as each light color reflects off of the sides of the mixer as it passes from input end 72 to the output end 74. Referring to FIG. 5B, mixer 73 can be tapered so that the fibers entering input end 72 can have a high NA while light guide 75 at output end 74 can have a low NA.

In this embodiment with LEDs each emitting one of a multiple colors, there is the advantage in that the number of green, red, and blue LEDs chosen can control the color temperature at the distal end of the light guide. Alternatively, adjusting the forward currents to each LED can also control the color temperature of the white light. In other configurations, choosing a lesser number of LEDs that emit a particular color can also be advantageous. A combination of both choosing the LEDS and adjusting the forward current can also change color temperature. For instance, in thoracic surgery where red color is dominant in the human cavity, an endoscopic solid-state light source that has less LEDs that emit red light into the endoscope is desired to create a proper contrast for the surgeon to distinguish features.

Figure 6:
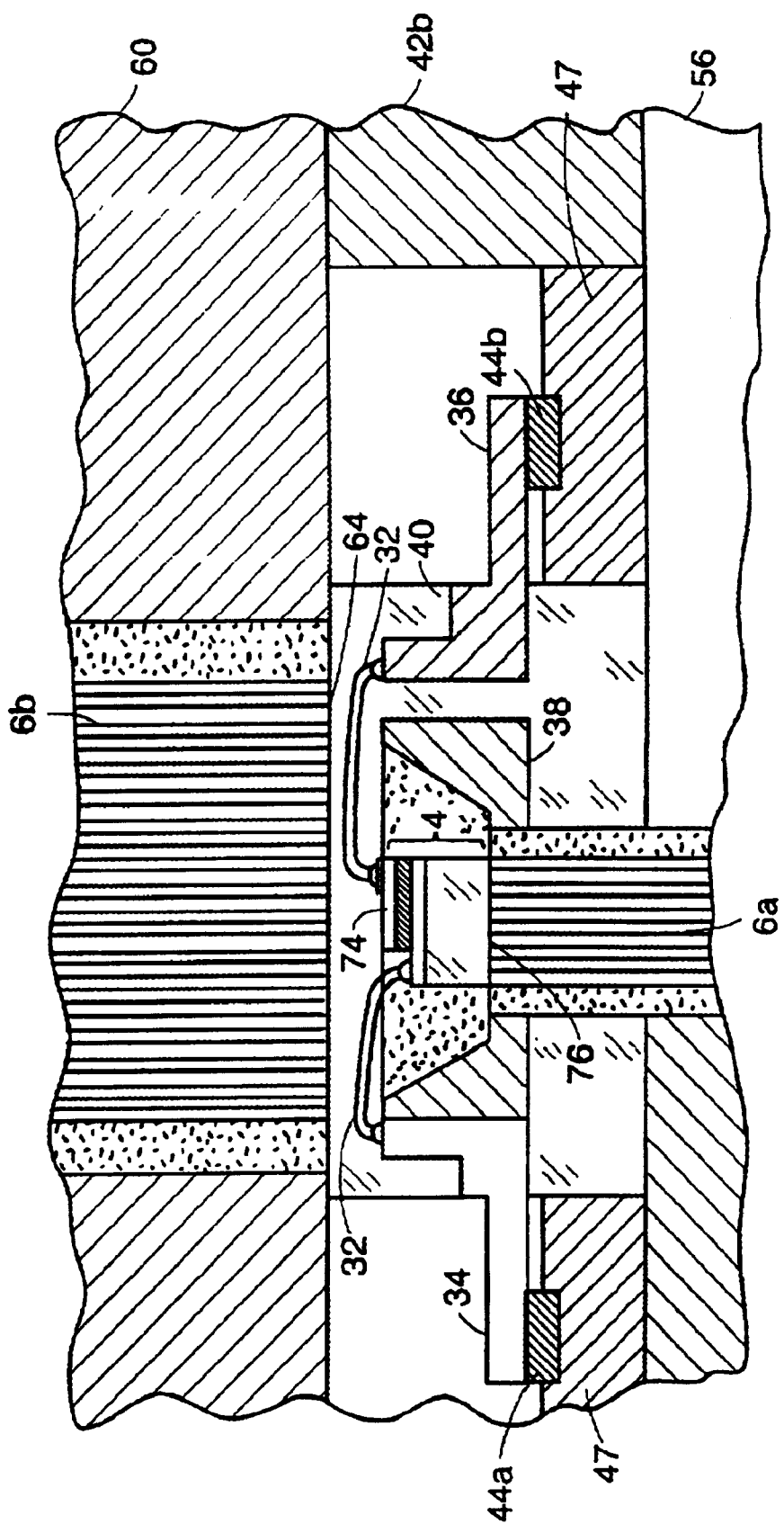
FIG. 6 is a cross-sectional view of an alternative embodiment of a solid-state light source.

Referring to FIG. 6, in other embodiments the epoxy encasement 40 can be modified differently. In this configuration, the top portion of epoxy casement 40 is polished down instead of drilled as in FIG. 3. The epoxy encasement is polished down such that its top surface is just above ohmic contacts 32. In this way, the thickness of the material of the encasement is minimized, but sufficiently thick to prevent damage to the ohmic contacts by the overlying fiber bundle. Fiber optic bundle 6b is also polished. Fiber optic bundle 6b and a top plate 60 are positioned so that each are flush with respect to each other. In other embodiments, the fiber end epoxy is replaced with ferrules. In still other embodiments, the ohmic contacts are not located at the top of the LED, so that the epoxy encasement can be polished down to the surface, thereby allowing the fiber optic bundle to be bonded directly to the top surface of the LED.

Figure 7A:
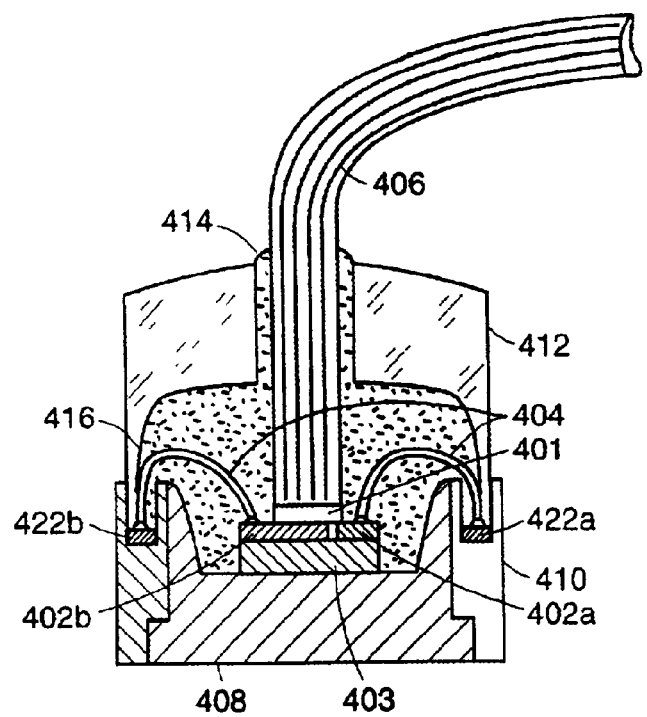
FIG. 7A is a cross-sectional view of another embodiment of the semiconductor light source.
Figure 7B:
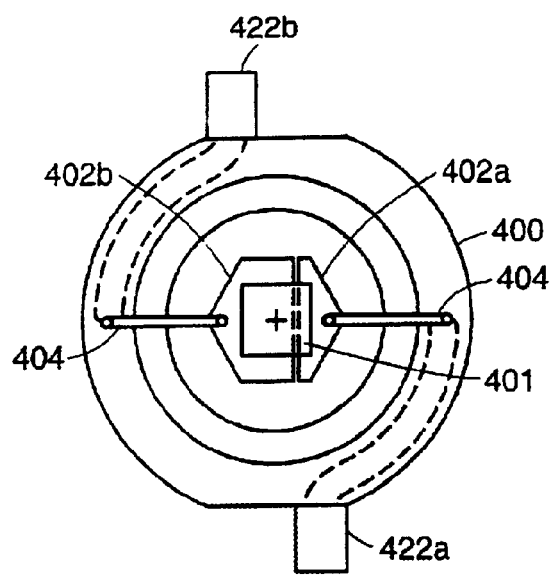
FIG. 7B is a top view of the semiconductor light source of FIG. 7A.

Referring to FIGS. 7A–7B, other LED configurations can be used in the solid-state light source. These configurations allow for the fiber optic bundle to come into contact with the surface of the LED without being obstructed by the ohmic contacts so that the maximum amount of light can be coupled into the fiber optic element. For instance, an LED 401, a flip-chip semiconductor device, is positioned on a fiber glass material 403. LED 401 is located within a reflector cup with reflective sides. Positioned between the fiber glass material 403 and LED 401 are two conductive terminals 402a and 402b which together form a hexagonal shape. Each terminal 402a and 402b is connected to a conductive bus 422a and 422b respectively via ohmic contacts 404. The positioning of conductive terminal 422a and 422b allows no obstructions on the surface of LED 401. A drill is used to bore through a plastic encasement 412 that protects the LEDs to form an aperture. A fiber optic bundle 406 is inserted through the aperture and through a silicone gel 416 onto or close to the surface of LED 401. An epoxy sealant 414 secures the fiber optic bundle 406 to plastic encasement 412. The LEDs suitable for this embodiment is manufactured by Lumileds Lighting of San Jose, Calif.

Figure 8C:
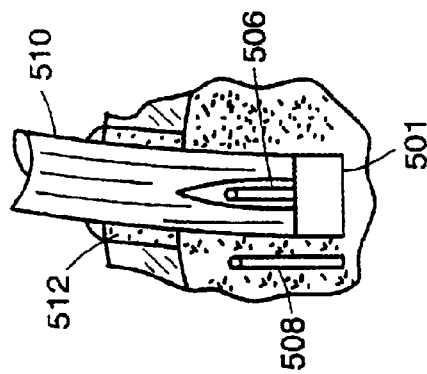
FIG. 8C is an enlarged cross-sectional view of FIG. 8A.
Figure 8B:
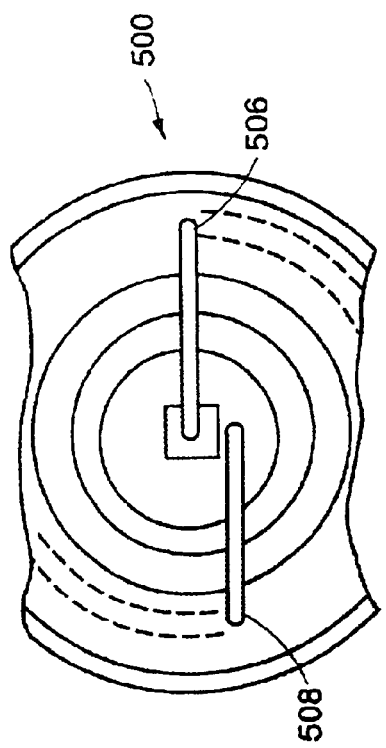
FIG. 8B is a top view of the semiconductor light source of FIG. 8A.
Figure 8A:
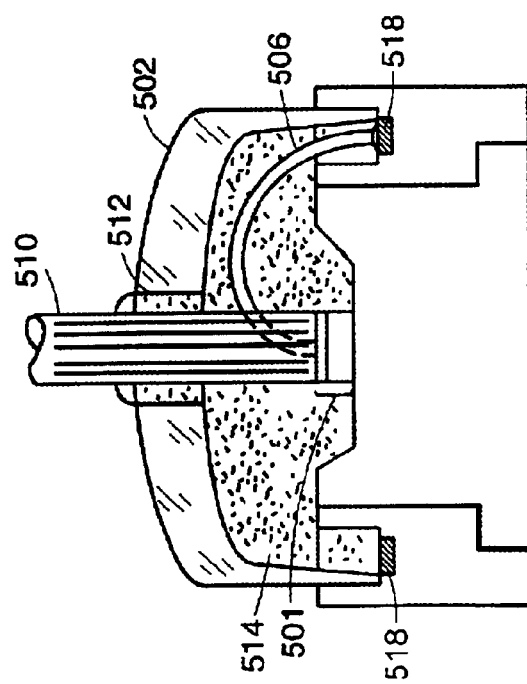
FIG. 8A is a cross-sectional view of another embodiment of the semiconductor light source.

Referring to FIGS. 8A–8C, other embodiments have one ohmic contact on the surface of an LED 501 that obstructs direct insertion of a fiber optic bundle 510 onto the surface of the LED. In these configurations, fiber optic bundle 510 is configured to attach to the LED. LED 501 is positioned on a reflector cup 516. An ohmic contact 508 connects the reflector cup to a conductive bus 516. A second ohmic contact 506 connects the top surface of LED 501 to a second conductive bus 518. Fiber optic bundle 510 is spliced so that fiber optic bundle 510 fits around ohmic contact 506. A drill is used to bore through a plastic encasement forming an aperture. Fiber optic bundle 510 is inserted through the aperture and through the silicone gel 514 and onto or close to the surface of LED 501. An epoxy 512 secures fiber optic bundle 514 to plastic encasement 502. Fiber optic bundle 504 fits around ohmic contact 506. The LEDs suitable for this embodiment is manufactured by Lumileds Lighting of San Jose, Calif.

In the above embodiments, the light receiving surfaces of the fiber optic bundles are positioned closely to the LEDs. However, other arrangements of semiconductor light sources and optical systems may be used.

Figure 9:
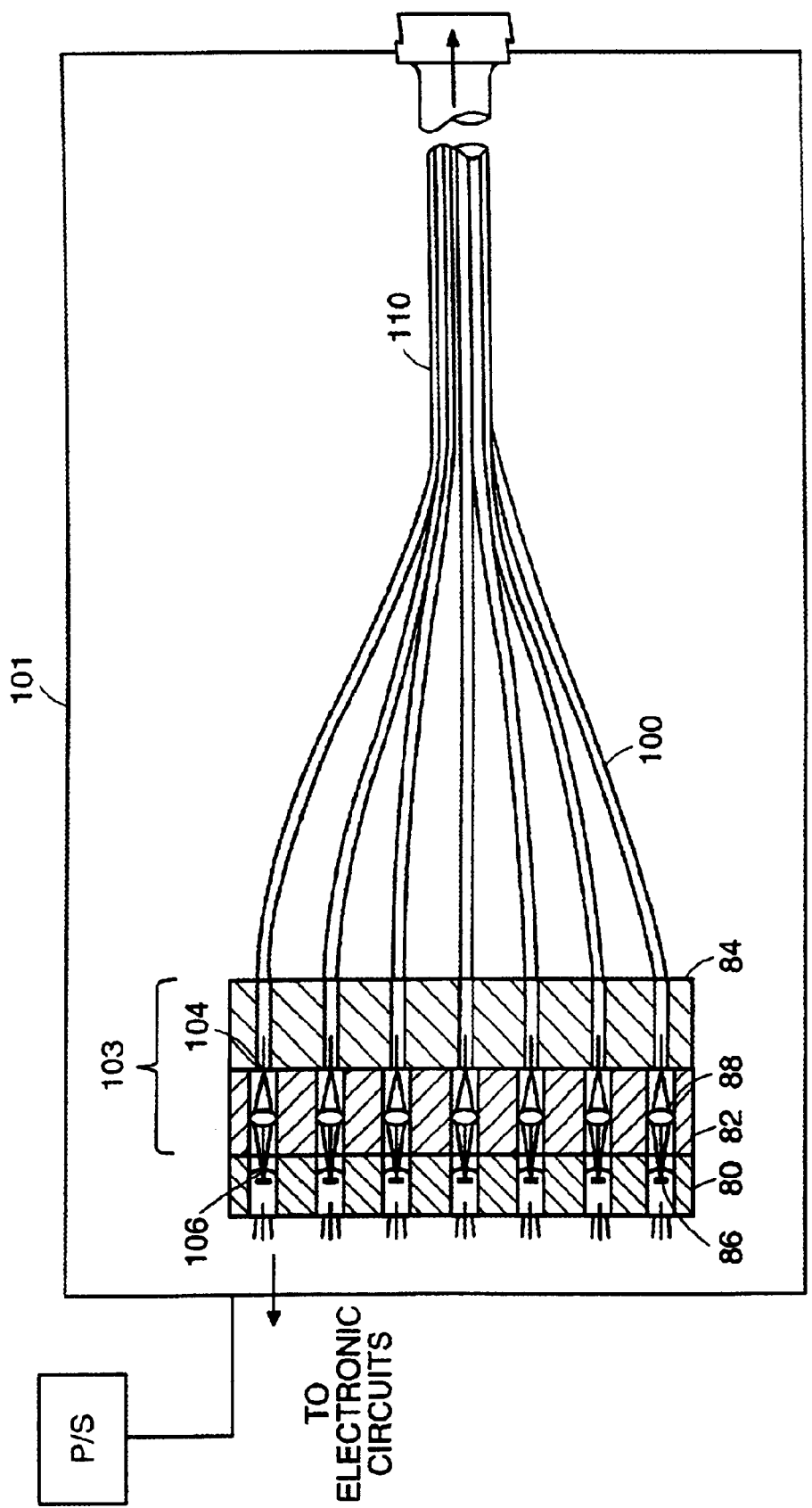
FIG. 9 is a cross-sectional side view of another embodiment of the solid-state light source.
Figure 10:
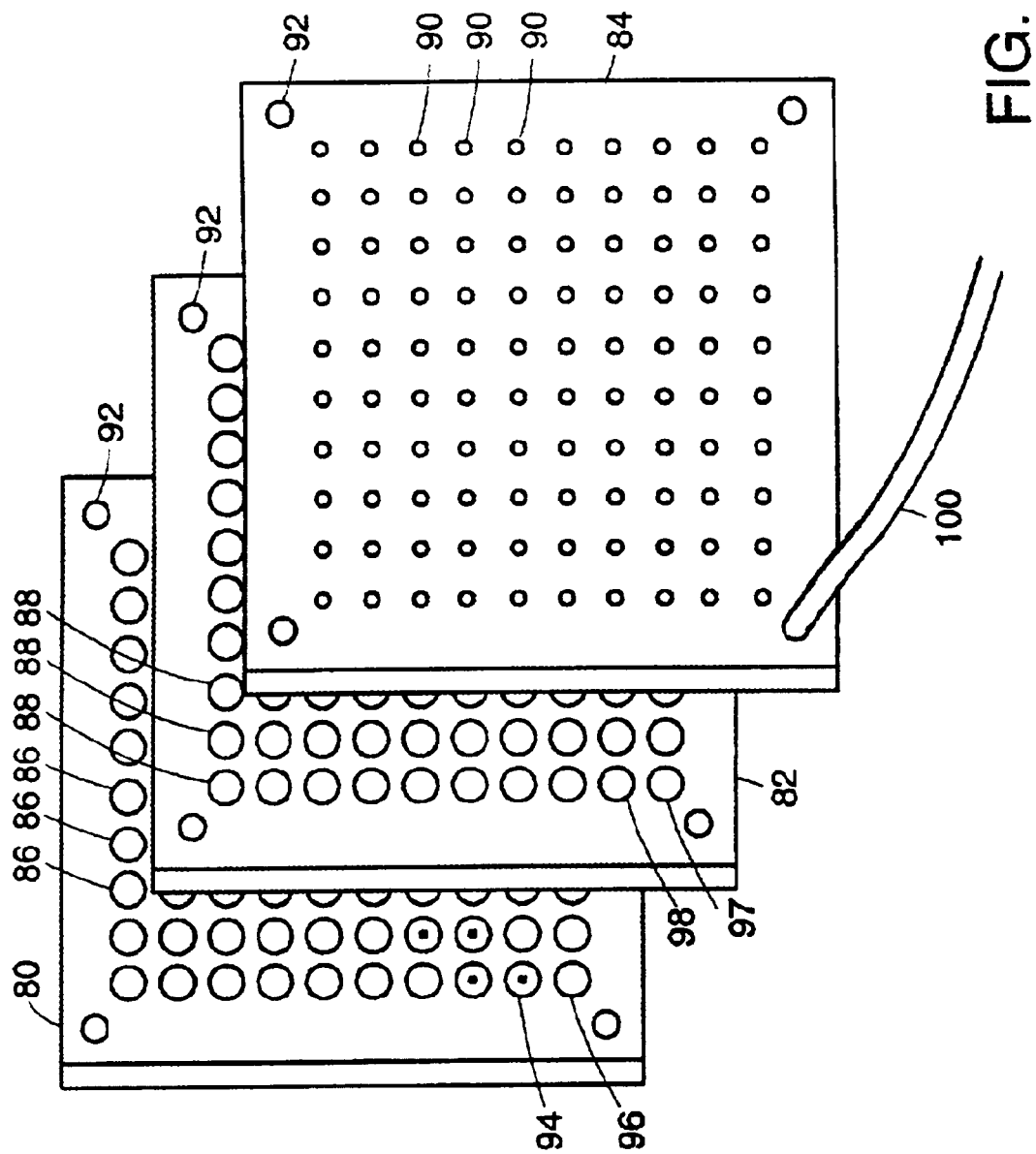
FIG. 10 is an exploded view of an LED plate, a lens plate, and a fiber line plate of FIG. 7.
Figure 11:
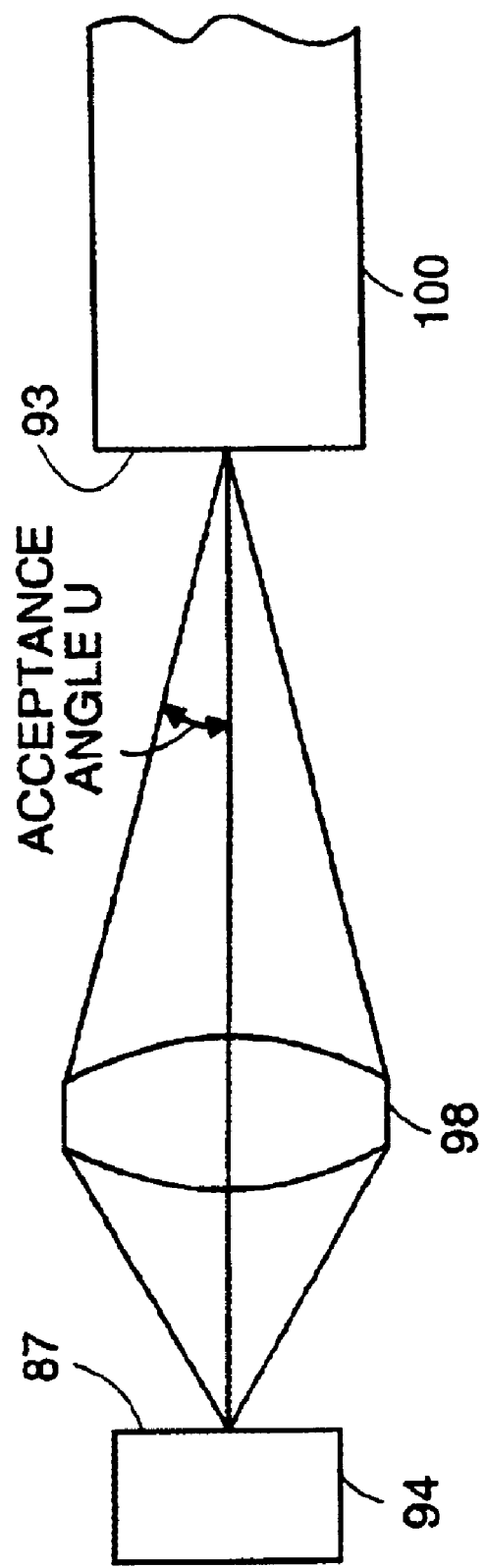
FIG. 11 is a schematic representation of one lens, one LED and one fiber line of FIGS. 7–8.

Referring to FIGS. 9–11, for example, a solid-state light source 101 includes an optical system 103 having a lens array 88 that receives light from a corresponding LED array 86 and focuses the light onto a corresponding aperture array 90. Aperture array 90 includes apertures each containing a fiber line 100.

LED array 86 includes a plate 80 having an array of openings 96. Each LED 94 is located within an opening 96. A second plate 82 similarly includes a lens array 88 that corresponds to each of the LEDs 94. Each lens 98 is located within an opening 98. A third plate 84 has a set of fiber optic lines 100 positioned within aperture array 90. Each fiber line 100 is aligned with a corresponding one of lenses 98.

Lens 98 and fiber line 100 are positioned to allow the maximum amount of light to be transferred from LED 94 to fiber line 100. Therefore, first plate 80 and second plate 82 are spaced such that the first plate is positioned so the active regions of LED 94 are at a first optical conjugate plane 106 (FIG. 10) of each lens 98. Likewise, third plate 84 and second plate 82 are spaced so that a second optical conjugate plane 104 of each lens 98 coincides with an entrance 93 of each of the corresponding fiber lines 100. Alignment holes 92 ensure that each corresponding LED 96, lens 98, and fiber line 100 remain properly aligned. Pins (not shown) are placed within each alignment hole to hold each plate in an aligned position.

Lenses 88 each have a working F-number, F, and each lens forms light beams at the image side of each lens with a numerical aperture, $NA_I$, so that $NA_I=1/(2F)$.

In order to maximize the light throughput of each fiber line 100, optical element 98 projects a light-emitting surface 87 of LED 94 onto an entrance face 93 of fiber line 100 so that the image of light-emitting surface 87 fully covers the entrance face 93. The numerical aperture in the image space, $NA_I$, is made equal or to slightly exceed the NA of fiber line 100, $NA_{lg}$. That is, $$NA_I \geq NA_{lg} = \sin u,$$

where u is the acceptance angle of the light guide.

In operation, when each LED 94 is powered, the light from each LED 94 emitted is received by a corresponding optical element 98. The optical element focuses the light on a corresponding fiber line 100. The combined light from each fiber line 100 is conveyed through a multi-bundle 110 to the light guide.

Figure 12:
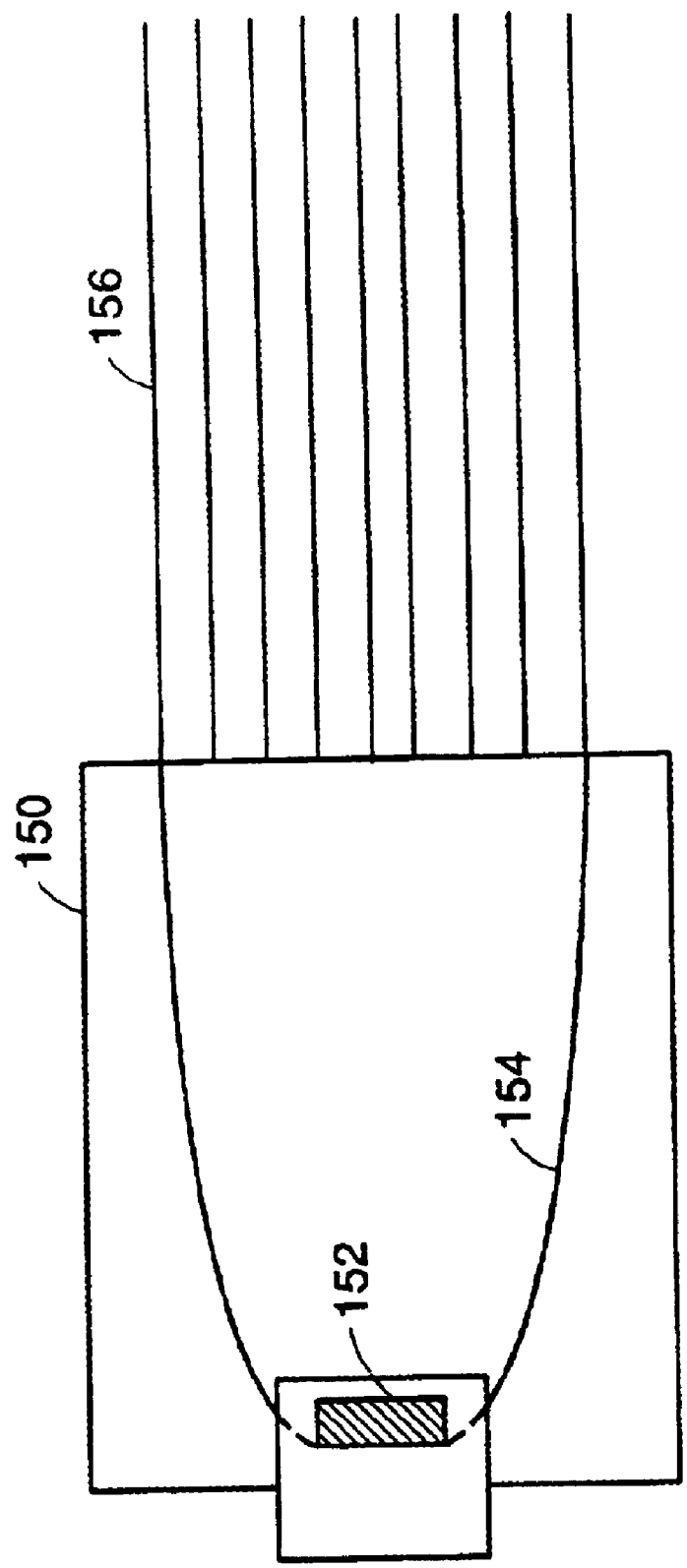
FIG. 12 is a cross sectional view of the LED with a light concentrator.

Referring to FIG. 12, a light concentrator 150 can be added to each LED 152 to reflect the light beams into fiber line 156. Light concentrator 150 has an internal cavity with a parabola shaped cross-section. In other embodiments, more complex shapes may be used. LED 152 is positioned in the interior of light concentrator 150. The interior surface 154 of light contractor 150 is mirrored. During operation, the light emitted from the sides of LED 42 are reflected off the interior surface 154 and reflected into fiber line 156. Thus, light concentrator 150 reflects light from the top surface of the LED and the sides. Other embodiments use a total internal reflection system. In those embodiments, the light concentrator is filled with a transparent dielectric material.

Figure 13A:
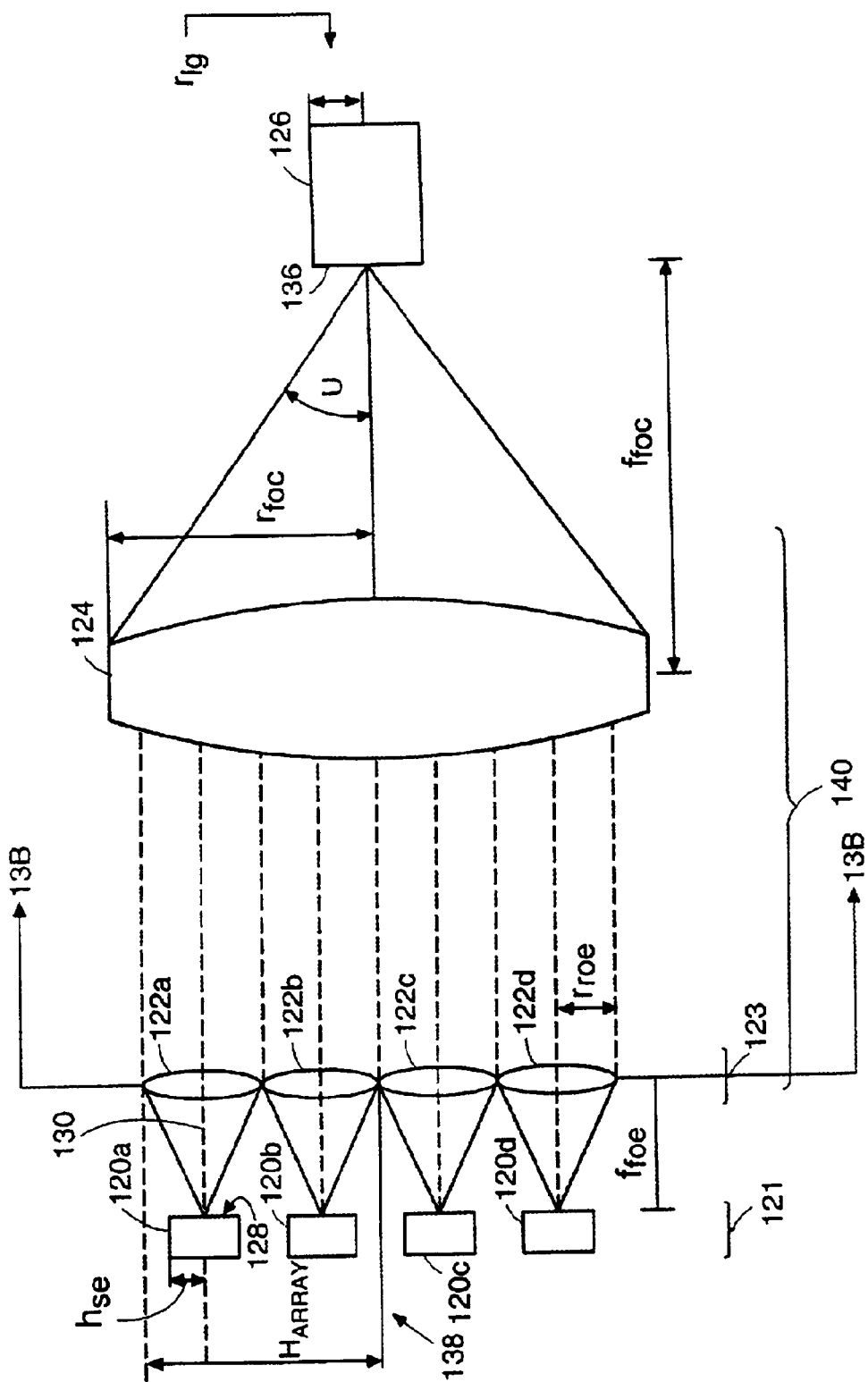
FIG. 13A is a schematic view of still another embodiment of a solid-state light source.
Figure 13B:
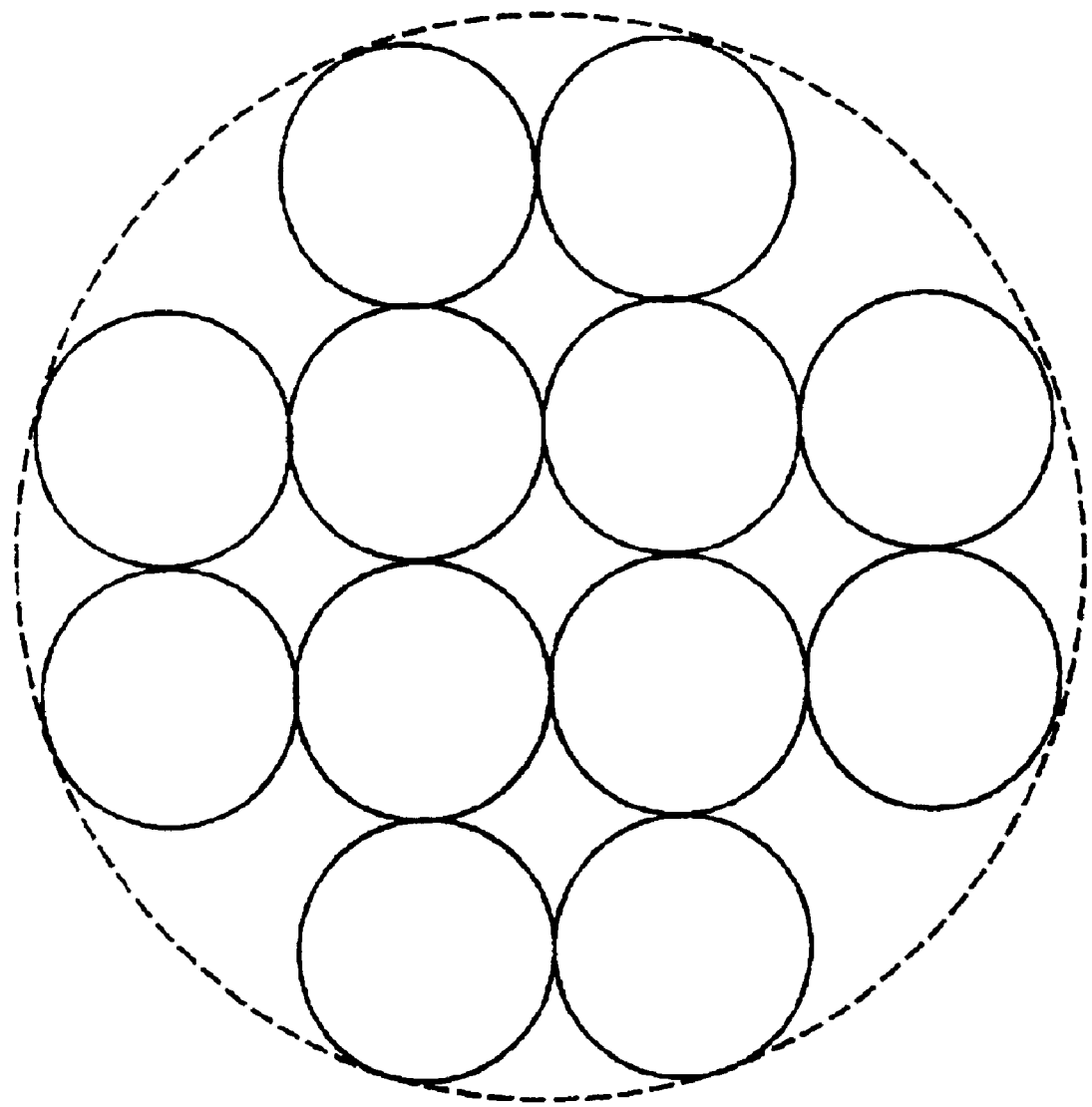
FIG. 13B is a schematic view of the circular-shaped lens array taken along lines 13B—13B of FIG. 13A.

Referring to FIGS. 13A and 13B, in another embodiment of a lens optical system such as optical system 140, a lens array 123 is used to collimate light from a corresponding LED array 121. A focusing lenses 124 then focuses the light onto a light guide 126.

LED array 121 is arranged in a circular-shaped two-dimensional array. Corresponding lens array 123 is located in front of LED array 121 so that each semiconductor light source 120 is positioned along an optical axis 130 of the corresponding lens 122. Lenses 122 collimate the light emitted by their corresponding LEDs 120. Lenses 122 may represent single lenses, such as single or double aspherics, compound lenses, gradient index (GRIN)-type lenses or combinations of each. In other embodiments, the lens array may be implemented as part of an LED array by means of adhesion, fusion etc. Other embodiments have a rectangular shaped LED and lens array.

In order to maintain a compact lens array configuration, the focal length of the lens, foe, and the diameter of the lens are chosen on the order of a few millimeters. The actual values are selected based on the size of LED emitting surface 128, which determines the field of view of lens 122. To collect the maximum amount of light emitted by LED 120, the F-number (ratio of the focal length to the aperture) of lens 122 is maintained as low as possible but within the cost constraints of lenses that are available and within the required design parameters to correct optical aberrations.

The collimated light from lens array 123 travels to a focusing lens 124. Focusing lens 124 projects the image of each LED light-emitting surface 128 on to an entrance face 136 of light guide 126. The image is magnified so that the size is approximately equal to entrance face 136 of light guide 126.

In this embodiment, focusing lens 124 is at least as large as LED array 121 or lens array 123. Also, the size of lens array 123 and focusing lens 124 are selected to be sufficiently large so that the image numerical aperture, $NA_I$, matches the NA of the light guide, $NA_{lg}$. The positions of lens array 123 and focusing lens 124 relative to the LEDs and light guide 126 is governed by the following relationship:

$$M = r_{lg}/h_{se} = f_{foc}/f_{oe}$$

where M is the magnification of optical system 140, $r_{lg}$ is the radius of light guide 126, $h_{se}$ is the height of LED 120 measured from optical axis 130, $f_{foc}$ is the focal length of 124 focusing lens, and foe is the focal length of lens 122, and $$\sin u = NA_I = NA_{lg} = H_{array}/f_{foc}$$

where $H_{array}$ is the height of LED array 121 measured from an axis 138 of focusing lens 124 to a top edge of the highest lens 122a.

By combining the previous equations, the maximum number of LEDs in the cross section containing optical axis 138 of focusing lens 124, n, can be determined as:

$$n = (f_{foc} \times NA_{lg})/r_{oe}$$

where $r_{oe}$ is the radius of the clear aperture lens 122.

For example, given a light guide 126 with an acceptance angle of 30 degrees, a light guide with a radius of 2.5 mm, LED 120 with a height of 0.125 mm, then the magnification, M, is 20. Given the focal length of lens 122 is 3 mm with an F-number equal to 1, then the radius of lens 122 is 1.5 mm and the focal length of focusing lens 124 is 60 mm. Thus, the maximum number of LEDs, n, is 20.

Figure 14:
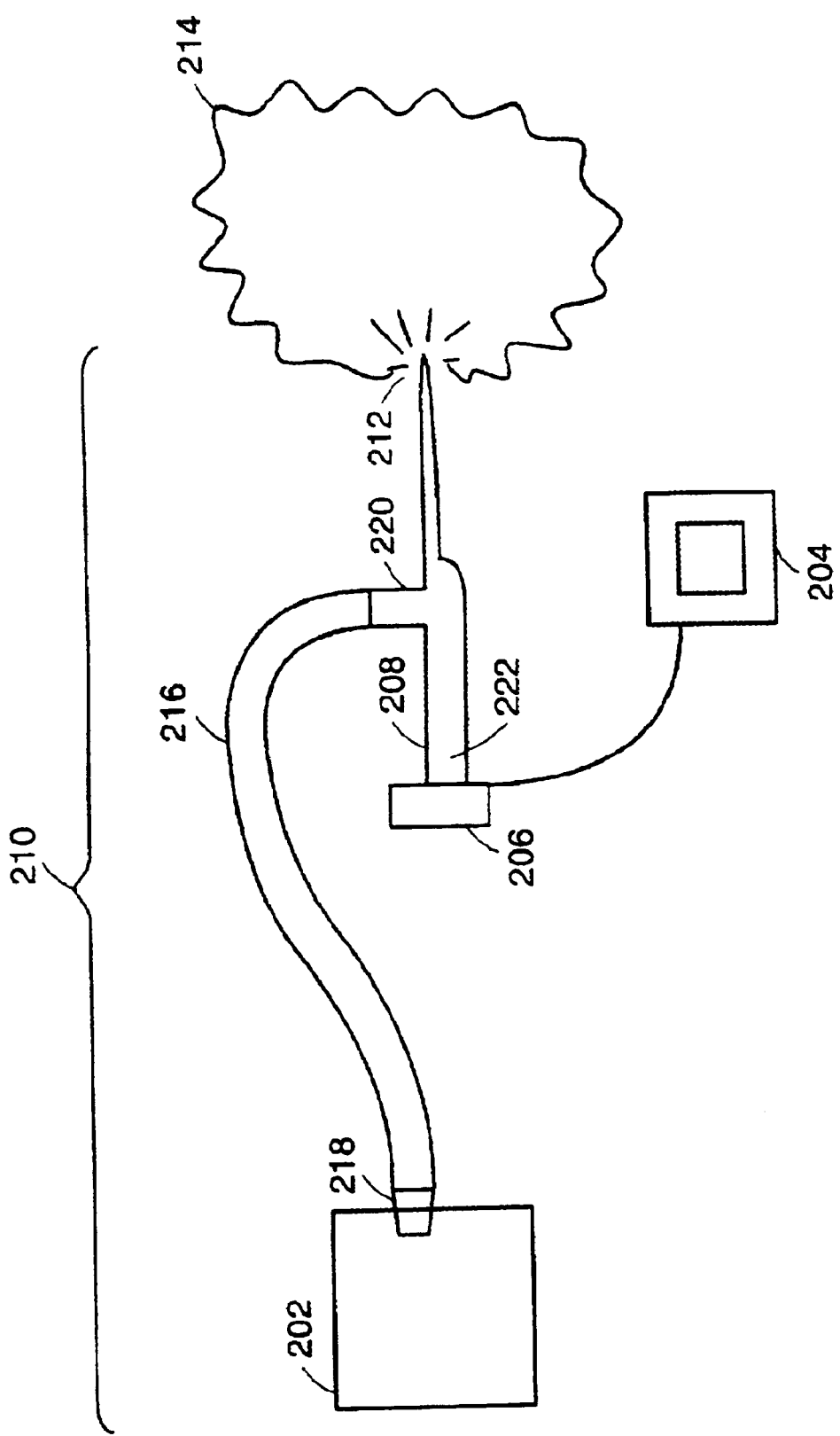
FIG. 14 is a block diagram of an endoscopic system having a solid-state light source for providing illumination.

Referring to FIG. 14, the solid-state light source can be used in an endoscopic system 210 to provide illumination. Endoscopic system 210 includes a solid-state light source 202, a video monitor 204, a camera 206, and an endoscope 208. Solid-state light source 202 generates white light that is conveyed to a distal end 212 of endoscope 208 via a light guide 216. Light guide 216 includes multiple fibers and is connected between an output connector 218 of light source 202 and a light post 220 of endoscope 208. The white light illuminates a working area 214 at distal end 212 of endoscope 208. A video camera 206, connected to a handle 222 of endoscope 208, generates video signals representative of images at a working area 214 for display on video monitor 204. Other embodiments have the solid-state light source directly connected to the handle 208 and emitting the light through the endoscope. This configuration eliminates light guide 216.

Figure 15A:
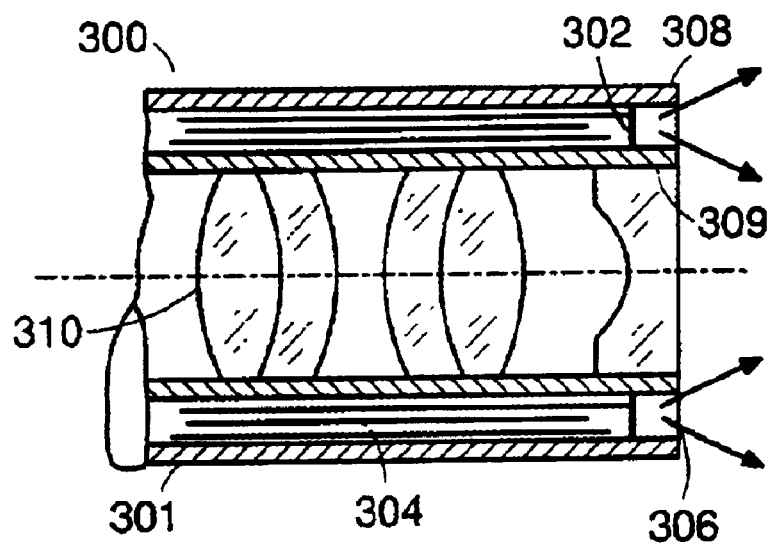
FIG. 15A is a cross-sectional side view of an endoscope with illuminating fiber lines in an annular arrangement.
Figure 15B:
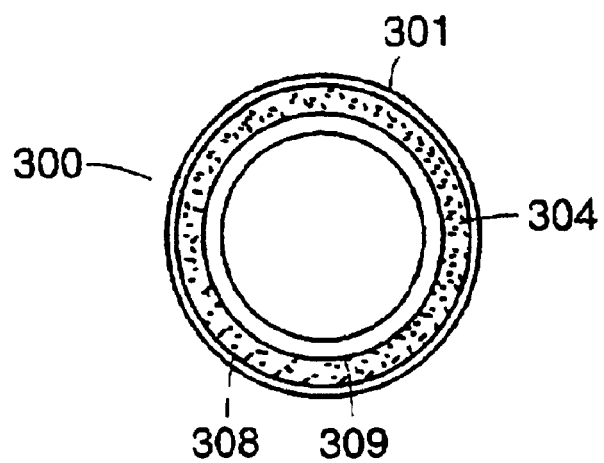
FIG. 15B is an end view of the endoscope of FIG. 15A.

In other solid-state source embodiments within an endoscopic system, referring to FIGS. 15A and 15B, light can travel within an endoscope 300 but near the circumference of a main shaft 301 of the endoscope. A group of fiber optic lines 304 travel from a handle of endoscope 300 (not shown) after receiving light from the semiconductor light sources. Fiber optic lines 304 extend to a distal end where each fiber optic line is connected to a phosphor layer 302. Each fiber optic line is tightly packed between an outer tube 308 which forms the exterior surface of endoscope 300 and an inner tube 309 which separates the fiber lines from an optic system 310 in the interior of the endoscope. A sapphire ring 306 is placed on top of phosphor ring 304 to protect phosphor layer 302 from damage.

Embodiments of the solid-state light source are not limited to endoscopes. For example, other embodiments of a solid-state light source can be found in flashlights, miner's helmets, microscopes, etc.

Other embodiments not described here are also within the scope of the following claims.

What is claimed is:

1. A solid-state light source for providing light to an endoscope, the solid-state light source comprising:

a plurality of semiconductor light sources for emitting light, each, semiconductor light source having an encasement that includes an aperture; and an optical system having an optical element having a proximal end, the optical system having an input for receiving emitted light from the semiconductor light sources, the optical system having an output for receiving transmitting light front the optical element, the output configured to be received by the endoscope, the optical system and the semiconductor light sources in aggregate providing an illumination path;

wherein each aperture receives an associated portion of the proximal end of the optical element and each associated portion is positioned to receive the light from the corresponding light emitting surface.

2. The solid-state light source of claim 1 wherein the optical element includes an optical fiber.

3. The solid-state light source of claim 1 wherein each semiconductor light source emits light to an optical fiber.

4. The solid-state light source of claim 3 wherein the optical fiber extends from each semiconductor light source to an interface of a light guide, the light guide extending to the output.

5. The solid-state light source of claim 1 wherein each semiconductor light source includes a light emitting diode (LED).

6. The solid-state light source of claim 1 wherein each semiconductor light source is configured to emit a blue light.

7. The solid-state light source of claim 1 wherein each semiconductor light source is configured to emit an ultraviolet light.

8. The solid-state light source of claim 1, further comprising a phosphor layer, the phosphor layer is located along the illumination path.

9. The solid-state light source of claim 8 wherein each semiconductor light source is in contact with the phosphor layer.

10. A solid-state light source for providing light to an endoscope, the solid-state light source comprising:

a plurality of semiconductor light sources for emitting light, each semiconductor light source having an encasement that includes an aperture;

an optical system having an optical element having a proximal end, the optical system having an input for receiving emitted light from the semiconductor light sources, the optical system having an output for receiving light from the optical element, the output configured to be received by the endoscope, the optical system and the semiconductor light sources in aggregate providing an illumination path;

wherein each aperture receives an associated portion of the proximal end of the optical element and each associated portion is positioned to receive the light from the corresponding light emitting surface; and a phosphor layer located along the illumination path wherein the phosphor layer is located at a distal end of the endoscope.

11. The solid-state light source of claim 1, further comprising a light concentrator positioned at the semiconductor light source, the light concentrator reflects light from at least one surface of the semiconductor light source.

12. The solid-state light source of claim 1 wherein each semiconductor light source includes a first light emitting diode (LED) configured to emit blue light, a second LED configured to emit red light and a third LED configured to emit green light, an overlapping light from each LED producing white light.

13. The solid-state light source of claim 12, further comprising a mixer positioned to receive light from the first LED, the second LED and the third LED and positioned to transmit the overlapping light to the fiber optic line.

14. The solid-state light source of claim 13 wherein each semiconductor light source includes a fourth LED configured to emit yellow light, the mixer receives light from the fourth LED.

15. The solid-state light source of claim 1 wherein each semiconductor light source includes a laser diode.

16. The solid-state source of claim 1 wherein each semiconductor light source includes a vertical cavity surface emission laser.

17. A solid-state light source for providing light to an endoscope, the solid-state light source comprising:

a semiconductor light source for emitting light; and an optical system having an optical element, the optical system having an input for receiving emitted light from the semiconductor light source, the optical system having an output for receiving light from the optical element, the output configured to be received by the endoscope, the optical system and the semiconductor light source in aggregate providing an illumination path;

wherein the semiconductor light source has a first surface and a second surface and is configured to emit light in opposite directions from the first surface and the second surface.

18. The solid-state light source of claim 17 wherein the first surface emits light to a fiber optic line and the second surface emits light to a second fiber optic line.

19. The solid-state light source of claim 18 wherein the semiconductor light source has a third surface and a fourth surface substantially perpendicular to the first surface, the semiconductor light source is configured to emit light in opposite directions from the third surface and the fourth surface, the third surface of the semiconductor light source configured to emit light to a third fiber optical line and the fourth surface of the semiconductor light source configured to emit light to a fourth fiber optical line.

20. The solid-state light source of claim 1 wherein the optical element is a fiber optic element; and further comprising:

a substantially transparent substance located within each encasement;

wherein the fiber optic element is inserted through the aperture and the substantially transparent substance.

21. The solid-state light source of claim 20 further comprising an ohmic contact positioned on a top surface of the semiconductor light source:

wherein the fiber optic element has a splice-end to receive the ohmic contact.

22. The solid-state light source of claim 1 wherein the optical system includes an array of lenses and a corresponding array of fiber optic lines.

23. The solid-state light source of claim 22 wherein the plurality of semiconductor light sources are in array and each semiconductor light source is optically aligned with a corresponding lens and each corresponding lens is optically aligned with a corresponding fiber optic lines.

24. The solid-state light source of claim 23 wherein each semiconductor light source is positioned in a first optical conjugate plane from the corresponding lens and each corresponding fiber optic line is positioned in a second optical conjugate plane from the corresponding lens.

25. The solid-state light source of claim 1 wherein the optical element includes:

an array of lenses configured to collimate light from a corresponding array of semiconductor light sources; and a focusing lens configured to focus a collimated light from the array of lenses.

26. The solid-state light source of claim 25 wherein the focusing lens focuses the collimated light onto a light guide.

27. The solid-state light source of claim 21, wherein the fiber optic element is positioned relative to the ohmic contact to ensure maximum light coupling efficiency.

28. The solid-state light source of claim 1, wherein the optical element comprises fibers having a rectangular-shaped cross-section conforming to a size and shape of the semiconductor source.

29. A system comprising:

an endoscope having a distal end, the endoscope comprising a phosphor layer positioned at the distal end along an illumination path, a semiconductor light source for emitting light; and an optical system having an optical element, the optical system having an input for receiving emitted light from the semiconductor light source, the optical system having an output for receiving light from the optical element, the output configured to be received by the endoscope, the optical system and the semiconductor light source in aggregate providing the illumination path.

30. The system of claim 29, wherein the semiconductor light source includes a light emitting diode (LED).

31. The system of claim 29, wherein the optical element includes an optical fiber.

32. A solid-state light source for providing light to an endoscope, the solid-state light source comprising:

a semiconductor light source of emitting light;

an optical system having an optical element, the optical system having an input for receiving emitted light from the semiconductor light source, the optical system having an output for receiving light from the optical element, the output configured to be received by the endoscope, the optical system and the semiconductor light source in aggregate providing an illumination path; and a phosphor layer positioned at the output of the optical system and along the illumination path.

33. The solid-state light source of claim 32, wherein the semiconductor light source includes a light emitting diode (LED).

34. The solid-state light source of claim 32, wherein the optical element includes an optical fiber.

* * * * *